United States Patent [19]
Ericsson

[11] Patent Number: 5,993,386
[45] Date of Patent: Nov. 30, 1999

[54] COMPUTER ASSISTED METHOD FOR THE DIAGNOSIS AND TREATMENT OF ILLNESS

[76] Inventor: Arthur Dale Ericsson, 6560 Fannin, Suite 720, Houston, Tex.

[21] Appl. No.: 08/893,026

[22] Filed: Jul. 15, 1997

[51] Int. Cl.⁶ ........................................................ A61B 5/00
[52] U.S. Cl. ............................................................ 600/300
[58] Field of Search ............................ 705/3, 2; 600/300, 600/301, 513

[56] References Cited

U.S. PATENT DOCUMENTS

| | | | |
|---|---|---|---|
| 5,255,187 | 10/1993 | Sorensen | 600/300 |
| 5,724,983 | 3/1998 | Selker et al. | 600/301 |
| 5,778,882 | 7/1998 | Raymond et al. | 600/513 |
| 5,842,175 | 11/1998 | Andros et al. | 705/3 |
| 5,845,253 | 12/1998 | Rensimer et al. | 705/2 |

*Primary Examiner*—Toe R. Swann
*Assistant Examiner*—Matthew Smithers
*Attorney, Agent, or Firm*—John R. Casperson

[57] ABSTRACT

A computerized technique for performing a medical outcomes analysis is disclosed including methods for quantifying a patients state of health to facilitate an increased quality of patient care and improving diagnostic techniques.

29 Claims, 1 Drawing Sheet

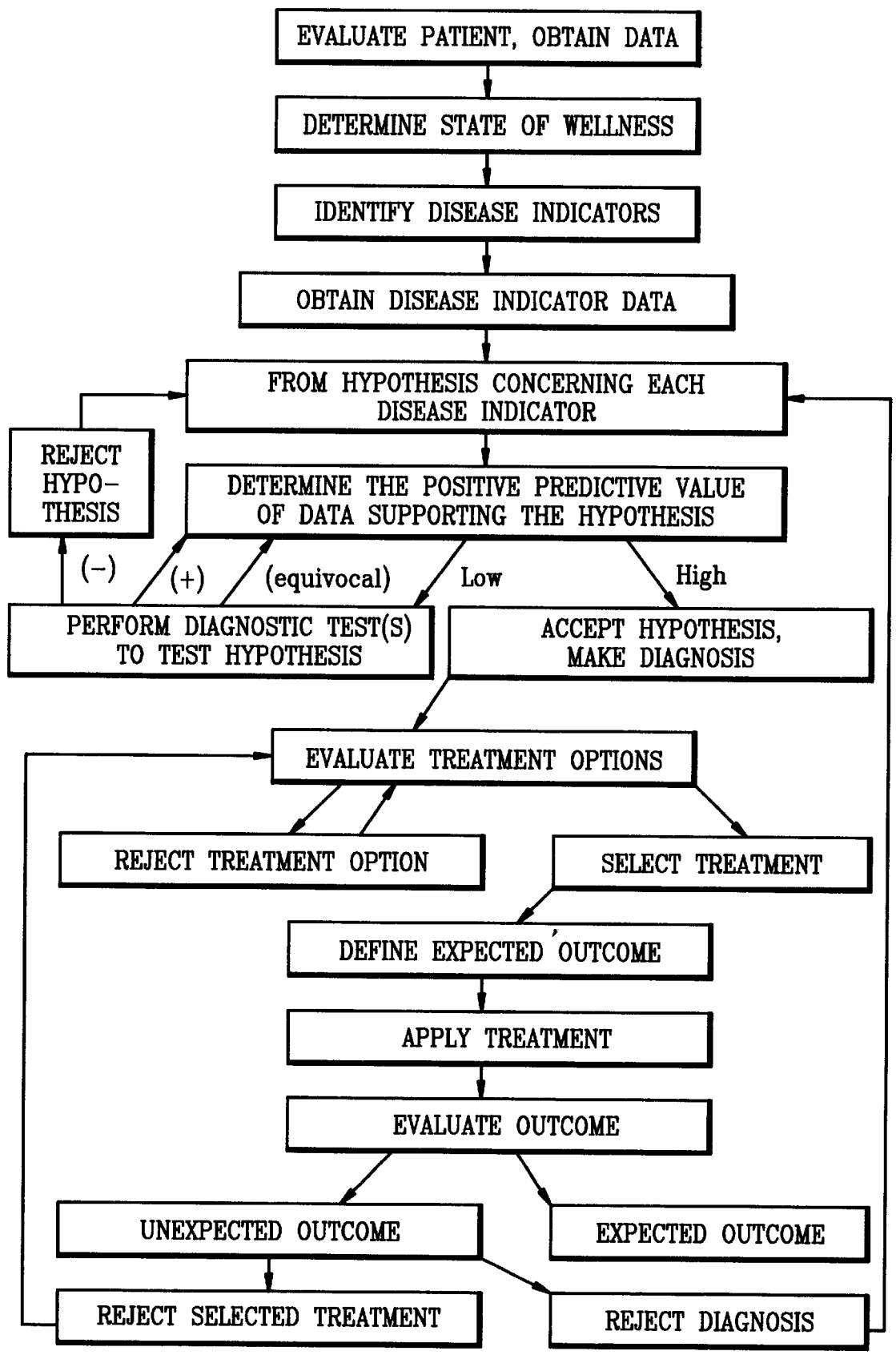

COMPUTER ASSISTED METHOD FOR THE DIAGNOSIS AND TREATMENT OF ILLNESS

BACKGROUND OF THE INVENTION

In one aspect, this invention relates to the use of computers to carry out methods useful in the practice of medicine. In another aspect, this invention relates to the use of computers to assist in the diagnosis and treatment of medical conditions. In another aspect, this invention relates to the use of computers to assist in managing patient care.

Computers are well suited for the analysis of outcomes. However, a computer program to perform medical outcomes analysis is not available. This is very unfortunate, because a medical outcomes analysis is vital for the prevention of development of illness, the improvement in the quality of care, the reduction of the costs of care, the restoration of health of the individual, and the prevention of the loss of useful work. A computer program to carry out an outcome analysis useful in the practice of medicine would be extremely desirable.

OBJECTS OF THE INVENTION

An object of this invention is to provide a computer program which is useful in the practice of medicine to promote the maintenance of health, to prevent illness, to treat illness, and to restore the individual to optimum health.

SUMMARY OF THE INVENTION

In accordance with the invention, numerical values are assigned to a patients state of health at different time. The method is carried out by determining a first state of health for a patient at a first time and assigning a first numeric value to the first state of health for the patient. An estimate is then made of an expected second state of health for a patient at or near a second time. The expected second state of health can be the same as or different from the first state of health. A numeric value is then assigned to the expected second state of health. At or near the second time, an actual second state of health for the patient is determined. A second numeric value is then assigned for the actual second state of health for the patient. A numeric value representative of error between the expected second state of health and the actual second state of health can then be established according to a predetermined relationship between the numeric value assigned to the expected second state of health and the numeric value assigned to the actual second state of health. The numeric values are selected from a range of numeric values which increase or decrease from a value corresponding to dead at one end of the range to normal at the other end of the range. This provides the mathematical predictability necessary to quantify the outcome and permit comparisons.

BRIEF DESCRIPTION OF THE DRAWINGS

FIG. 1 illustrates a process for the diagnosis and treatment of illness which is well suited for carrying out the invention.

DETAILED DESCRIPTION OF THE INVENTION

Application of the invention is based on the recognition of several key factors.

A functional disturbance follows a predictable course over time and these outcomes are related to the onset, course and observation state and the outcome of therapy. This disturbance may become manifest in the analysis of the predictors and wellness/illness.

The accuracy of the analysis is enhanced by the application of scientific analysis of both diagnosis and treatment.

Movement of the individual by degrees of freedom is predictable and may be subjected to mathematical analysis.

Altered physiological function may be measured and thus quantified in both health and disease—often by measuring the systematic alterations.

Interception by therapy and/or altering behavior can and will alter function and thereby enhance and prolong viable health of the individual.

This system may be monitored and feed back may be used to modify the interventions(s) necessary for the maintenance of health and/or to correct the state of illness.

In order to develop a numerical measurement of the ordered states of health, it was elected to utilize a discrete time Markovian process which governs the movement of one state to another. It was reasoned that the different states of health, represent different states within the system/time. Moreover, it was assumed that each person will move through these states in an orderly step-wise and not totally random fashion. Analysis of time/outcome is, therefore, a function of movement along the scale of numeric values, which provides the mathematical predictability that is necessary for any outcomes analysis.

In accordance with the invention, numerical values are assigned to a patients state of health at different times. The method is carried out by determining a first state of health for a patient at a first time and assigning a first numeric value to the first state of health for the patient. With reference to the FIGURE, this can be done at the block labeled "DETERMINE STATE OF WELLNESS". An estimate is then made of an expected second state of health for a patient at or near a second time. With reference to the FIGURE, this can be done at the block labeled "DEFINE EXPECTED OUTCOME". The expected second state of health can be the same as or different from the first state of health. A numeric value is then assigned to the expected second state of health. At or near the second time, an actual second state of health for the patient is determined. This can be done at the block labeled "EVALUATE OUTCOME". A second numeric value is then assigned for the actual second state of health for the patient. A numeric value representative of error between the expected second state of health and the actual second state of health can then be established according to a predetermined relationship between the numeric value assigned to the expected second state of health and the numeric value assigned to the actual second state of health.

Generally speaking, the numeric value for state of health increases or decreases from dead at one end of the range to normal at the other end of the range according, to the criteria shown in the following Table:

TABLE I

STATES OF HEALTH

| State of Health | Criteria |
| --- | --- |
| dead | Lifeless |
| moribund | support mandatory, progressing rapidly |
| pre-moribund. | Very sick, active support necessary. Severe signs and/or symptoms of disease. Laboratory tests abnormal. |
| Severely Disabled | critically unstable, hospitalization indicated, laboratory abnormal. Death is not imminent. |
| Disabled | requiring of special care and assistance. Signs and symptoms severe, laboratory abnormal. |
| moderately disabled | clinical signs and symptoms of disease, requires assistance and frequent medical care, laboratory abnormal |
| mildly disabled | clinical signs and symptoms of disease, requiring of some assistance, able to care for needs, laboratory abnormal |
| impaired | clinical signs and symptoms of disease, cares for self needs, Unable to perform normal activity, laboratory abnormal |
| mildly impaired | some clinical signs and symptoms of disease, able to carry on normal activity with effort, laboratory may be abnormal |
| pre-impaired | minor clinical signs and symptoms of disease, able to carry on normal activity, laboratory may be abnormal |
| abnormal | appears normal, no complaints, no clinical evidence of disease, laboratory may be abnormal |
| normal | Normal, no complaints, no evidence of disease, clinical and laboratory normal. |

However, the criteria can be modified in accordance with the invention, or states of health added or deleted from Table I, and still provide extremely useful information. The guiding criteria is the recognition that an individual's progress from normal to dead is a continuum and that the numerical values corresponding to states along the continuum should follow an increasing or decreasing order, to permit mathematical treatment. The numeric values are thus selected from a range of numeric values which increase or decrease from a value corresponding to dead at one end of the range to normal at the other end of the range. Preferably, the values incrementally increase from dead to normal because this permits simple mathematical treatment, such as by subtraction, to provide a difference value which is clearly related by + or − sign to obtaining a results are better or worse than expected. For example, integer values from 0 to 11 can be assigned to the states shown in Table I. The values can be input as such into a computer, or assigned by the computer in response to clicking a button or other hot area on the computer screen which designates a state of health, with a mouse or other device, which in turn signals the computer to retrieve the predetermined value for the hot area for subsequent storage.

With reference again to FIG. 1, it is generally necessary to formulate a diagnosis for the patient, such as in the box labeled "ACCEPT HYPOTHESIS. MAKE DIAGNOSIS". An intervention plan is then selected for the patient, usually with input from the patient, which is appropriate for the diagnosis. This can be done at the box labeled "SELECT TREATMENT". The selected plan is then executed prior to the second time.

The estimate of the expected second state of health made at the box labeled "DEFINE EXPECTED OUTCOME" is based in part on a presumed correctness of the diagnosis made at the box "ACCEPT HYPOTHESIS, MAKE DIAGNOSIS" and/or on the presumed effectiveness of the intervention plan selected at the box labeled "SELECT TREATMENT". The estimate is, of course, also largely influenced by the pathogenesis of the disease process affecting the patient as well as other factors as discussed herein.

To enable additional patient-related information to be retrieved and studied, it is generally necessary to input into the computer code representative of the identity of the patient as well as other pertinent admission-type information. This can be done at the box labeled "EVALUATE PATIENT, OBTAIN DATA". To enable closer comparisons to be made as to the different outcomes between similar patients, it is also generally desirable to input into the computer a code representative of the diagnosis for the patient, such as at the box labeled "ACCEPT HYPOTHESIS, MAKE DIAGNOSIS". The code, can be entered manually or generated by the computer such as in response to a mouse click on a window hot spot which generates a predetermined code. Similarly, it can be desirable to input into the computer a code representative of the intervention plan for the patient, such as at the box labeled 'SELECT TREATMENT". Other information, such as the costs of formulating the diagnosis for the patient at the box labeled "ACCEPT HYPOTHESIS, MAKE DIAGNOSIS", and the costs the costs of executing the intervention plan at the box labeled "APPLY TREATMENT" can also be usefully employed to construct a computer database to enable subsequent cost and effectiveness comparisons. To enable quality of care comparisons, code representative of the identities of the physician(s) who formulated the diagnosis at the box labeled "ACCEPT HYPOTHESIS, MAKE DIAGNOSIS" and the intervention plan at the box labeled 'SELECT TREATMENT" can also be input.

Symptoms and their observable physiological counterpart, signs, occur in the course of the evolving process of all organic interactions, including the maintenance of health and development of disease. In the first place, all signs/symptoms may arise form either a linear response or non-linear physiological response. It is conceivable that a specific symptom/sign may be the direct result of the organ/organism damage; Linear. In this case, the sign/symptom is the immediate and direct result of the physiological disturbance. On the other hand, most symptoms/signs arise, not from the direct insult or damage, but rather from an attempt, by the organism to establish homeostasis in the face of abnormality. This process may be very complex but it allows the organism to function in a changing internal/external environment. This process is called Non-linear.

Most pathological processes produce linear and non-linear signs simultaneously and since the organism functions in an environment in time as these symptoms/signs are continually changing.

An analysis of the onset of symptoms in all patients reveals that they may occur suddenly (Acute), more gradually, over weeks or months, (Sub-Acute), and slowly, over years, (Chronic).

These symptoms, that have appeared, will either abate (Improve), get worse (Progress) or remain unchanged (Static) over a period of time that the therapist has established. This period of time may be defined in terms of days, weeks, months, years or decades.

The signs/symptoms that the patient is able to demonstrate at the time of evaluation, by the doctor, is that of localized (Focal) disease, afflicts several different areas (Multifocal) and/or is totally non-localized (Diffuse). Each of the symptoms/signs listed may be modified with the above onset, time course and locality specific modifying adjectives.

It follows that a great deal of information relevant to the ultimate diagnosis can be obtained by determining whether the onset of the disease indicator was acute, subacute or chronic; determining whether the disease indicator has followed an abated, progressive or static course, and determining by examination whether the disease indicator is focalized, multifocal or diffuse. To facilitate the diagnosis of disease early on, it is generally desirable to obtain this information from patients which display a sign or symptom of disease near the beginning of the care process, such as at the box labeled 'OBTAIN DISEASE INDICATOR DATA". This information can be related to disease pathogenesis possibilities by the following Table.

TABLE II

DISEASE PATHOGENESIS POSSIBILITIES

| ONSET | COURSE | EXAM | PATHOGENESIS |
|---|---|---|---|
| Acute | abated | focalized | infectious, traumatic, vascular |
| | | Multifocal | infectious |
| | | Diffuse | infectious |
| | Progressive | focalized | infectious, allergic, iatrogenic |
| | | Multifocal | infectious, allergic |
| | | Diffuse | infectious, external toxin, allergic |
| | Static | focalized | infectious |
| | | Multifocal | infectious |
| | | Diffuse | infectious |
| Subacute | abated | focalized | infectious, electrophysiological |
| | | Multifocal | infectious |
| | | Diffuse | infectious |
| | Progressive | focalized | infectious, allergic, autoimmune, neoplasm, iatrogenic, electrophysiological |
| | | Multifocal | infectious, allergic, autoimmune, neoplasm, idiopathic |
| | | Diffuse | infectious, external toxin, metabolic, allergic, idiopathic |
| | Static | focalized | infectious, electrophysiological |
| | | Multifocal | infectious |
| | | Diffuse | infectious |
| Chronic | abated | focalized | infectious, electrophysiological |
| | | Multifocal | infectious |
| | | Diffuse | infectious |
| | Progressive | focalized | infectious, degenerative, autoimmune, neoplasm, electrophysiological |
| | | Muitifocal | infectious, degenerative, autoimmune, neoplasm, idiopathic |
| | | Diffuse | infectious, hereditary/genetic, |

TABLE II-continued

DISEASE PATHOGENESIS POSSIBILITIES

| ONSET | COURSE | EXAM | PATHOGENESIS |
|---|---|---|---|
| | | | external toxin, metabolic, idiopathic |
| | Static | focalized | infectious, electrophysiological |
| | | Multifocal | infectious |
| | | Diffuse | infectious, hereditary/genetic |

In a preferred embodiment of the invention, at least one disease pathogenesis possibility is assigned to each patient which displays a disease indicator. This can be manually, by use of the Table, or, more preferably, by a computer which makes the assignments in response to user input on three selected hot spots or buttons.

The assigned disease pathogenesis possibilities can be output from the computer and used to facilitate hypothesis formation at the box labeled "FORM HYPOTHESIS CONCERNING EACH DISEASE INDICATOR", as well as for a subsequent quality check of the diagnosis made at the box labeled 'ACCEPT HYPOTHESIS, MAKE DIAGNOSIS". To carry out this latter aspect of the invention, the previously mentioned code representative for the diagnosis of the patient is associated, such as by a look-up table, with its pathogenesis, preferably, from among those listed in Table II and an assignment made. The assigned disease pathogenesis is compared with the previously derived pathogenesis possibilities From Table II and an output generated from the computer listing any disease pathogenesis possibility which is different from the assigned disease pathogenesis.

As previously mentioned, the expected outcome defined at the box labeled "DEFINE EXPECTED OUTCOME" is largely influenced by disease pathogenesis, and/or the selected treatment, or lack thereof. It can also be influenced on a case by case basis by patients having multiple abnormalities. The outcome possibilities, generally described as "Better", "Unchanged" or "Worse", and their relationship to individual disease pathogenesis is given by Table III.

TABLE III

OUTCOME POSSIBILITIES

| BETTER | UNCHANGED | WORSE |
|---|---|---|
| infectious | hereditary/genetic infectious | Infectious |
| traumatic | | |
| Toxic (external) | | Toxic (external) |
| Metabolic (internal) | | Metabolic (internal) |
| | | Vascular |
| | | Degenerative |
| Allergic | | |
| | | Autoimmune |
| | | Neoplasm |
| | Idiopathic | |
| | Iatrogenic | |
| | Electrophysiological | electrophysiological |

Because of the multiple factors at play in estimating outcome, it is preferred to utilize an individual patient profile with assigned interactive number, with the predictable outcomes for each abnormality with any therapy or other intervention defined and determined. The estimate of outcome made at the box labeled "DEFINE EXPECTED OUTCOME" is preferably, however, based at least in part on the outcome possibilities listed. The association between pathogenesis and outcome is preferably made by computer, and can be based on either the initial input of disease data at the box labeled "OBTAIN DISEASE INDICATOR DATA", or the disease pathogenesis associated with the diagnosis made at the box labeled "ACCEPT HYPOTHESIS, MAKE DIAGNOSIS".

Where the outcome is unexpected, as illustrated at the box labeled "UNEXPECTED OUTCOME", the correlations in Table III can be used in some instances to reject the diagnosis as illustrated at the box labeled "REJECT DIAGNOSIS". This is preferably done after a period of time which is appropriate for the specific altered physiology. Where the second state of health as measured at the box labeled "EVALUATE OUTCOME" is determined to be unexpectedly better, unchanged or worse than the first state of health, the determination can be associated with a plurality of disease pathogenesis possibilities from the Table of Outcome Possibilities, and an output generated from the computer of disease pathogenesis possibilities from the Table of Outcome possibilities which are different from the disease pathogenesis of the diagnosis. This information can be used to further formulate hypotheses at the box labeled "FORM HYPOTHESIS CONCERNING EACH DISEASE INDICATOR". In a similar manner, an output can be generated from the computer of disease pathogenesis possibilities generated from the Table of Outcome possibilities which are different from disease pathogenesis possibilities derived from the Table of Disease Pathogenesis Possibilities. Each patient's treatment, especially where the outcome is unexpected, can be modified by analysis of the outcome versus the model system.

The Markovian analysis can be defined by the probability matrices p(k) and the probability of going from one step to another is P(k)(ij) and this can be estimated by diagnostic category (k) onset from state (I). When the probability of either alternative is sufficiently high and the list of alternative sis limited (3), then the probability may be stated as the probability equal to the number of outcomes favorable to the hypothesis divided by the total number of outcomes. When the outcomes are unrelated then one can calculate the standard deviation and arrive at a probability with a confidence of 95%. This standard deviation is equal to the square root of number of trials multiplied by probability of success and/or failure. Using a computer model of physiological testing as a standard then actual patient data may be correlated to this standard and predicted outcomes will demonstrate a variance from the expected norm.

From the above, facilitation of this system will allow for more effective and timely diagnosis and treatment for each individual patient (outpatient and in hospital patient). Obviously, the greatest impact would be on hospitalized patients, where daily delays are not only costly, but account for errors diagnosis and treatment. Prediction of a patients course of treatment is extremely valuable for cost containment and capitation. Each treatment pattern besides representing a configuration of services also represents a specific cost level. This translates into a more efficient and effective program of diagnosis and therapy and better utilization of hospital and clinical services.

In most cases, it is only necessary for a skilled clinician to formulate a few hypothesis at the box labeled "FORM HYPOTHESIS CONCERNING EACH DISEASE INDICATOR". Executing the step given at the box labeled "DETERMINE THE POSITIVE PREDICTIVE VALUE OF DATA SUPPORTING THE HYPOTHESIS" is often much more problematic, although it can be relatively straightforward, such as where a patient with a history of ear aches or sinus infections complains of same and the examination results are consistent with such a diagnosis. Two tools which may be used to execute the step given at the box are the Chi Square Analysis and Bayes theorem.

The Chi Square Analysis requires that the diagnostician/ therapist effect a hypothesis of the patients symptoms. There is a null hypothesis for every hypothesis that is effected. The methodology is as follows:

For each decision there must be facts which support that decision (+) or facts that reject that hypothesis (−). The assumption is that for every hypothesis there is a null hypothesis in order of weighted probability and there are only a limited number of possibilities that merit hypothesis formation.

A 2×2 matrix for the large scale results of a particular diagnostic test (or other data set) is constructed as follows:

TABLE IV

| Test Results | True Disease Status: | |
|---|---|---|
| | Diseased | Nondiseased |
| Positive | # true positive | # false positive |
| Negative | # false negative | # true negative |

The answer to the question "If the test results are positive, what is the probability that the patient has the disease?" is given by: Positive Predictive value=# true positive/total positives (i.e. # true positive/(#true positive+#false positive). However, for a population with a low prevalence of disease, there is a large number of false positives and a small number of false negatives, whereas for a population with a high prevalence of disease, there is a smaller number of false positives and a higher number of false negatives. The positive predictive value of a test is thus higher where the population has been selected to display other indicators of the disease, to give the particular disease a higher prevalence in that particular population, however, at a greater risk of error from negative test results. The false positive error rate can also be reduced by reducing the sensitivity of the test, which will result in a higher false negative error rate, or by increasing the specificity of the test, also resulting in a higher false negative error rate. It must be kept in mind, however, that the identification, diagnosis and proper treatment of individuals who display false positive (alpha error) or false negative (beta error) results is remains critical. If desired, the Chi square analysis can also be used to answer to the questions "If the test results are positive, what is the probability that the patient does not have the disease?" by the relationship # false positive/total positives (i.e. # false positive/(#true positive+#false positive) and "If the test results are negative, what is the probability that the patient nevertheless has the disease?" by the relationship=# false negative/total negative (i.e. # false negative/(#true negative+#false negative).

Application of the invention provides an excellent technique for constructing matrices from populations having a higher incidence of the disease in question in a quantifiable way to thereby increase the positive predictive value of a positive test result. In accordance with this aspect of the invention, the population selected for construction of the Chi Square matrix for a particular test are preferably characterized by the same set of determinations of whether the onset of the disease indicator was acute, subacute or chronic, whether the disease indicator has followed an abated, progressive or static course, and whether the disease indicator is focalized, multifocal or diffuse. The database is constructed by inputting into the computer codes representative of a specific test, the results of the specific test, positive or negative, f or each patient, and code representative of a determination made such as at the block labeled "EVALUATE OUTCOME" of whether the test results were true positive, false positive, false negative, or true negative. The necessary algorithms are easily produced by those skilled in the art.

The Chi Square concept can be further refined as Bayes' theorem. This mathematical model relies upon the Chi Square hypothesis for conceptualization and is given by the formula:

$$p(D+|T+)=p(T+|D+)p(D+)/(p(T+|D+)p(D+))+(p(T+|D-)p(D-))$$

wherein p denotes probability,

D+ means that the diagnosis is correct;

D– means that the diagnosis is not correct,

T+ means that a certain diagnostic test for the diagnosed condition is positive;

T– means that the test is negative;

and the symbol | means "conditional upon" what immediately follows.

As with the Chi Square analysis, the positive predictive value of a test is enhanced wherein D+ is estimated based on the incidence of the disease in question among a large population of patients having similar signs and symptoms, such as patients characterized by the same set of determinations of whether the onset of the disease indicator was acute, subacute or chronic, whether the disease indicator has followed an abated, progressive or static course, and whether the disease indicator is focalized, multifocal or diffuse. The estimation of D+ from a computerized database selecting such patients is thus a preferred technique for increasing the positive predictive value of any test, as well as determining the probability of an erroneous test result.

Once a sufficiently large database has been accumulated, the analysis can be modified to provide a predictive value of a numerical test result obtained for a particular patient.

Normally, a positive predictive value in the range of 90 to 950% is desired, since selecting a numerical value to give a higher probability increases the risk of a particular test result being categorized such that it is a false negative. For a condition which carries a dire consequence, such as death, from a false negative test result, it can be desirable to select a numerical value for the dividing the test results into a negative or positive test result such that the probability of a false negative test result is extremely low, such as less than 1%. To carry out this embodiment of the invention, a database of numerical test results and their classification as true positive, false positive, false negative, and true negative based on the outcomes analysis from diagnosis and treatment is accumulated in association with the determinations of whether the onset of the disease indicator was acute, subacute or chronic; whether the disease indicator has followed an abated, progressive or static course, and whether the disease indicator is focalized, multifocal or diffuse, preferably together with additional risk factor data such as patient age, family history of the disease in question, other test results, etc. The numerical results of the particular test required to provide the predetermined certainty for a patient having the same characterizing data set is then calculated from the database and the actual results for the particular patient then compared to the calculated number and characterized as positive or negative.

While certain preferred embodiments of my invention have been described herein, the invention is not to be construed as so limited, except to the extent such limitations are found in the claims.

What is claimed is:

1. A method for using a computer to monitor the diagnosis and treatment of illness, said method comprising evaluating a patient;

determining a first state of health for the patient at a first time, assigning a first numeric value to the first state of health for the patient and inputting such value to the computer, estimating an expected second state of health for a patient at or near a second time, wherein the expected second state of health can be the same as or different from the first state of health, assigning a numeric value to the expected second state of health and inputting such value to the computer, determining an actual second state of health for the patient at or near the second time, assigning a second numerical value to the actual second state of health for the patient and inputting such value to the computer, establishing, by use of the computer, a numeric value representative of error between the expected second state of health and the actual second state of health according to a predetermined relationship between the numeric value assigned to the expected second state of health and the numeric value assigned to the actual second state of health, wherein the numeric values are selected from a range of numeric values which increase or decrease from a value corresponding to dead at one end of the range to normal at the other end of the range, and wherein the numeric value representative of error quantifies an outcome useful for evaluating the diagnosis and treatment of the patient.

2. A method as in claim 1 wherein the numeric value for state of health increases or decreases from dead at one end of the range to normal at the other end of the range according to the criteria shown in the following Table:

TABLE

STATES OF HEALTH

| State of Health | Criteria |
|---|---|
| dead | Lifeless |
| moribund | support mandatory, progressing rapidly |
| pre-moribund | Very sick, active support necessary. Severe signs and/or symptoms of disease. Laboratory tests abnormal. |

TABLE-continued
STATES OF HEALTH

| State of Health | Criteria |
| --- | --- |
| Severely Disabled | critically unstable, hospitalization indicated, laboratory abnormal. Death is not imminent. |
| Disabled | requiring of special care and assistance. Signs and symptoms severe, laboratory abnormal. |
| moderately disabled | clinical signs and symptoms of disease, requires assistance and frequent medical care, laboratory abnormal |
| mildly disabled | clinical signs and symptoms of disease, requiring of some assistance, able to care for needs, laboratory abnormal |
| impaired | clinical signs and symptoms of disease, cares for self needs, Unable to perform normal activity, laboratory abnormal |
| mildly impaired | some clinical signs and symptoms of disease, able to carry on normal activity with effort, laboratory may be abnormal |
| pre-impaired | minor clinical signs and symptoms of disease, able to carry on normal activity, laboratory may be abnormal |
| abnormal | appears normal, no complaints, no clinical evidence of disease, laboratory may be abnormal |
| normal | Normal, no complaints, no evidence of disease, clinical and laboratory normal. |

3. A method as in claim 2 wherein the numeric values assigned to state of health incrementally increase from dead to normal.

4. A method as in claim 2 wherein the numeric values assigned to state of health incrementally decrease from dead to normal.

5. A method as in claim 2 wherein the numeric values assigned to state of health are assigned by a computer based on a user input.

6. A method as in claim 1 further comprising
    formulating a diagnosis for the patient,
    selecting an intervention plan for the patient which is appropriate for the diagnosis, and
    executing the intervention plan prior to the second time.

7. A method as in claim 6 further comprising
    estimating the expected second state of health based in part on a presumed correctness of the diagnosis.

8. A method as in claim 6 further comprising
    estimating the expected second state of health based in part on a presumed effectiveness of the intervention plan.

9. A method as in claim 6 further comprising
    estimating the expected second state of health based in part on a presumed correctness of the diagnosis and a presumed effectiveness of the intervention plan.

10. A method as in claim 1 further comprising
    estimating an expected second state of health for a patient at or near a second time, wherein
    the expected second state of health can be the same as or different from the first state of health.

11. A method as in claim 6 further comprising
    inputting into a computer a code representative of the identity of the patient,
    inputting into a computer a code representative of the diagnosis for the patient, and
    inputting into a computer a code representative of the intervention plan for the patient.

12. A method as in claim 11 further comprising
    inputting into a computer a code representative of the costs of formulating the diagnosis for the patient, and
    inputting into a computer a code representative of the costs of executing the intervention plan.

13. A method as in claim 12 further comprising
    inputting into a computer a code representative of the identity of a physician who has formulated the diagnosis, and
    inputting into a computer a code representative of the identity of a physician who has formulated the intervention plan.

14. A method for using a computer to monitor the diagnosis and treatment of illness of a patient, wherein the patient displays a disease indicator, said method comprising
    evaluating the patient,
    determining whether the onset of the disease indicator was acute, subacute or chronic,
    determining whether the disease indicator has followed an abated, progressive or static course,
    determining by examination whether the disease indicator is focalized, multifocal or diffuse,
    determining a first state of health for the patient at a first time
    assigning a first numeric value to the first state of health for the patient and inputting such value to the computer,
    estimating an expected second state of health for a patient at or near a second time, wherein the expected second state of health can be the same as or different from the first state of health,
    assigning a numeric value to the expected second state of health and inputting such value to the computer,
    determining an actual second state of health for the patient at or near the second time,
    assigning a second numerical value to the actual second state of health for the patient and inputting such value to the computer,
    establishing, by use of the computer, a numeric value representative of error between the expected second state of health and the actual second state of health according to a predetermined relationship between the numeric value assigned to the expected second state of health and the numeric value assigned to the actual second state of health,
    wherein the numeric values are selected from a range of numeric values which increase or decrease from a value corresponding to dead at one end of the range to normal at the other end of the range, and wherein the numeric value representative of error quantifies an outcome useful for evaluating the diagnosis and treatment of the patient.

15. A method as in claim 14 further comprising, assigning, for a patient which displays a disease indicator, at least one disease pathogenesis possibility based on the determinations of whether the onset of the disease indicator was acute, subacute or chronic, whether the disease indicator has followed an abated, progressive or static course, and whether the disease indicator is focalized, multifocal or diffuse, as given by the following Table:

TABLE

DISEASE PATHOGENESIS POSSIBILITIES

| ONSET | COURSE | EXAM | PATHOGENESIS |
|---|---|---|---|
| Acute | abated | focalized | infectious, traumatic, vascular |
|  |  | Multifocal | infectious |
|  |  | Diffuse | infectious |
|  | Progressive | focalized | infectious, allergic, iatrogenic |
|  |  | Multifocal | infectious, allergic |
|  |  | Diffuse | infectious, external toxin, allergic |
|  | Static | focalized | infectious |
|  |  | Multifocal | infectious |
|  |  | Diffuse | infectious |
| Subacute | abated | focalized | infectious, electrophysiological |
|  |  | Multifocal | infectious |
|  |  | Diffuse | infectious |
|  | Progressive | focalized | infectious, allergic, autoimmune, neoplasm, iatrogenic, electrophysiological |
|  |  | Multifocal | infectious, allergic, autoimmune, neoplasm, idiopathic |
|  |  | Diffuse | infectious, external toxin, metabolic, allergic, idiopathic |
|  | Static | focalized | infectious, electrophysiological |
|  |  | Multifocal | infectious |
|  |  | Diffuse | infectious |
| Chronic | abated | focalized | infectious, electrophysiological |
|  |  | Multifocal | infectious |
|  |  | Diffuse | infectious |
|  | Progressive | focalized | infectious, degenerative, autoimmune, neoplasm, electrophysiological |
|  |  | Muitifocal | infectious, degenerative, autoimmune, neoplasm, idiopathic |
|  |  | Diffuse | infectious, hereditary/genetic, external toxin, metabolic, idiopathic |
|  | Static | focalized | infectious, electrophysiological |
|  |  | Multifocal | infectious |
|  |  | Diffuse | infectious, hereditary/genetic. |

16. A method as in claim 15 wherein the at least one disease pathogenesis possibility is assigned by a computer based on user input of codes representative of the onset of the disease indicator was acute, subacute or chronic, whether the disease indicator has followed an abated, progressive or static course, and whether the disease indicator is focalized, multifocal or diffuse.

17. A method as in claim 16 further comprising inputting into a computer a code representative of the diagnosis for the patient, associating such code representative of the diagnosis for the patient with a disease pathogenesis selected from the group consisting of hereditary/genetic, infectious, traumatic, toxic (external), metabolic (internal), vascular, degenerative, allergic, autoimmune, neoplasm, idiopathic, iatrogenic, and electrophysiological, by use of the computer, assigning a disease pathogenesis to the diagnosis for the patient by use of the computer, comparing the assigned disease pathogenesis with the at least one disease pathogenesis possibility, and generating an output from the computer listing any disease pathogenesis possibility which is different from the assigned disease pathogenesis.

18. A method as in claim 16 further comprising inputting into a computer a code representative of the diagnosis for the patient, associating such code representative of the diagnosis for the patient with a disease pathogenesis selected from the group consisting of hereditary/genetic, infectious, traumatic, toxic (external), metabolic (internal), vascular, degenerative, allergic, autoimmune, neoplasm, idiopathic, iatrogenic, and electrophysiological, by use of the computer, associating the disease pathogenesis with at least one outcome possibility given by the following Table:

TABLE

OUTCOME POSSIBILITIES

| BETTER | UNCHANGED | WORSE |
|---|---|---|
| infectious | hereditary/genetic infectious | Infectious |
| traumatic |  |  |
| Toxic (external) |  | Toxic (external) |
| Metabolic (internal) |  | Metabolic (internal) |
|  |  | Vascular |
|  |  | Degenerative |
| Allergic |  |  |
|  |  | Autoimmune |
|  |  | Neoplasm |
|  | Idiopathic |  |
|  | Iatrogenic |  |
|  | Electrophysiological | electrophysiological | and estimating the expected second state of health based in part on the at least one outcome possibility.

19. A method as in claim 18 further comprising determining whether the actual second state of health is better, unchanged or worse than the first state of health, associating the determination of whether the actual second state of health is better, unchanged or worse than the first state of health with a plurality of disease pathogenesis possibilities from the Table of Outcome Possibilities, generating an output from the computer of disease pathogenesis possibilities from the Table of Outcome possibilities which are different from the disease pathogenesis of the diagnosis.

20. A method as in claim 19 further comprising generating an output from the computer of disease pathogenesis possibilities generated from the Table of Outcome possibilities which are different from disease pathogenesis possibilities derived from the Table of Disease Pathogenesis Possibilities.

21. A method as in claim 6 further comprising performing a diagnostic test on the patient, obtaining a positive test result from the diagnostic test; and determining a probability that the formulated diagnosis for the patient is correct.

22. A method as in claim 21 wherein probability is estimated based on a Chi Square analysis.

23. A method as in claim 22 wherein the Chi Square analysis is performed by computer based on data obtained from a population of patients characterized by the same set of determinations of whether the onset of the disease indicator was acute, subacute or chronic, whether the disease indicator has followed an abated, progressive or static course, and whether the disease indicator is focalized, multifocal or diffuse.

24. A method as in claim 22 further comprising inputting into the computer codes representative of a specific diagnostic test, the results of the specific diagnostic test, positive or negative, for each patient, and code representative of a determination of whether the test results were true positive, false positive, false negative, or true negative.

25. A method as in claim 21 wherein the probability is determined according to the formula $$p(D+|T+)=p(T+|D+)p(D+)/(p(T+|D+)p(D+))+(p(T+|D-)p(D-))$$

wherein p denotes probability;

D+ means that the diagnosis is correct;

D− means that the diagnosis is not correct;

T+ means that a certain diagnostic test for the diagnosed condition is positive;

T− means that the test is negative;

and the symbol | means "conditional upon" what immediately follows.

26. A method as in claim 25 wherein D+ is estimated based on the incidence of the disease in question among a large population of patients having similar signs and symptoms.

27. A method as in claim 26 wherein D+ is estimated from a computerized database.

28. A method as in claim 21 further comprising inputting into a computer a code representative of the identity of a physician who has formulated the diagnosis.

29. A method as in claim 24 further comprising inputting into the computer codes representative of the numerical value of the results of a specific diagnostic test, accumulating in the computer a database of numerical test results and their classification as true positive, false positive, false negative, and true negative; calculating from the database the numerical results of a particular test which is required to provide a predetermined certainty of result for a patient having a selected set of characterizing data; and characterizing the actual test results for a particular patient as positive or negative in comparison to the calculated number.

* * * * *